United States Patent
Perassinoto et al.

(10) Patent No.: US 10,485,748 B2
(45) Date of Patent: Nov. 26, 2019

(54) COMPOSITION COMPRISING CYCLODEXTRIN AS UV- AND IR-RADIATION SCREEN AGENT

(71) Applicant: ISP INVESTMENTS INC., Wilmington, DE (US)

(72) Inventors: Nelson Luís Perassinoto, SãPaulo (BR); Maria Regina Bartuccio Raponi, SãPaulo (BR); Juliana Luri Yoshida Shitara, SãPaulo (BR); Tatiana Miyashiro Kumayama, SãPaulo (BR)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 14/780,672

(22) PCT Filed: Apr. 1, 2014

(86) PCT No.: PCT/US2014/032458
§ 371 (c)(1),
(2) Date: Sep. 28, 2015

(87) PCT Pub. No.: WO2014/165471
PCT Pub. Date: Oct. 9, 2014

(65) Prior Publication Data
US 2016/0051459 A1   Feb. 25, 2016

(30) Foreign Application Priority Data
Apr. 3, 2013 (BR) .......................... 10 20130079693

(51) Int. Cl.
| | | |
|---|---|---|
| *A61K 8/73* | (2006.01) | |
| *A61Q 17/04* | (2006.01) | |
| *A61K 8/06* | (2006.01) | |
| *A61K 8/37* | (2006.01) | |
| *A61K 8/40* | (2006.01) | |

(52) U.S. Cl.
CPC .............. *A61K 8/738* (2013.01); *A61K 8/062* (2013.01); *A61K 8/37* (2013.01); *A61K 8/40* (2013.01); *A61Q 17/04* (2013.01); *A61K 2800/41* (2013.01); *A61K 2800/596* (2013.01)

(58) Field of Classification Search
CPC ................ A61K 8/738; A61K 2800/41; A61K 2800/596; A61K 8/062; A61K 8/37; A61K 8/40; A61Q 17/04
See application file for complete search history.

(56) References Cited

U.S. PATENT DOCUMENTS

| | | | | |
|---|---|---|---|---|
| 4,869,897 A * | 9/1989 | Chatterjee | ................ | A61K 8/40 424/47 |
| 5,756,484 A * | 5/1998 | Fuertes | ................ | C08B 37/0012 424/464 |
| 5,821,237 A | 10/1998 | Bissett et al. | | |
| 6,458,192 B1 * | 10/2002 | Tsujio | .................... | C09D 11/18 106/31.32 |
| 6,703,032 B2 * | 3/2004 | Gers-Barlag | ............ | A61K 8/06 424/401 |
| 7,396,400 B2 * | 7/2008 | Nakamura | ............. | C09D 11/16 106/31.58 |
| 2002/0110570 A1 | 8/2002 | Gers-Barlag et al. | | |
| 2003/0130231 A1 * | 7/2003 | Regiert | .................. | A61K 8/678 514/58 |
| 2004/0234479 A1 * | 11/2004 | Schleifenbaum | ........ | A21D 2/00 424/70.13 |
| 2005/0250737 A1 * | 11/2005 | Hughes | ................ | A61K 9/0048 514/58 |
| 2005/0271598 A1 * | 12/2005 | Friedman | ............... | A61K 8/046 424/47 |
| 2007/0155695 A1 | 7/2007 | Wirth et al. | | |
| 2008/0089852 A1 | 4/2008 | Hotz et al. | | |
| 2012/0130031 A1 | 5/2012 | Swanzy | | |

OTHER PUBLICATIONS

Loftsson, What are cyclodextrins?, http://www.eurocdsoc.com/index.php?option=com_content&view=article&id=67:what-are-cyclodextrins&catid=37:article, acquired online May 2016.*
Munoz-Ruiz et al (International Journal of Pharmaceutics, vol. 148, 1997, pp. 33-39) (Year: 1997).*
International Search Report, PCT/US2014/032458 published on Oct. 9, 2014.

* cited by examiner

*Primary Examiner* — Mark V Stevens
(74) *Attorney, Agent, or Firm* — William J. Davis; Nathalie Tietcheu

(57) ABSTRACT

The present invention relates to cosmetic compositions comprising cyclodextrin as UV- and IR-radiation screen agent, and skin treatments wherein such compositions are spread upon the skin or hair of the subject to be treated. The present invention further relates to the use of cyclodextrin as booster for filtering UV radiation in compositions comprising chemical and physical UV radiation filters.

9 Claims, 1 Drawing Sheet

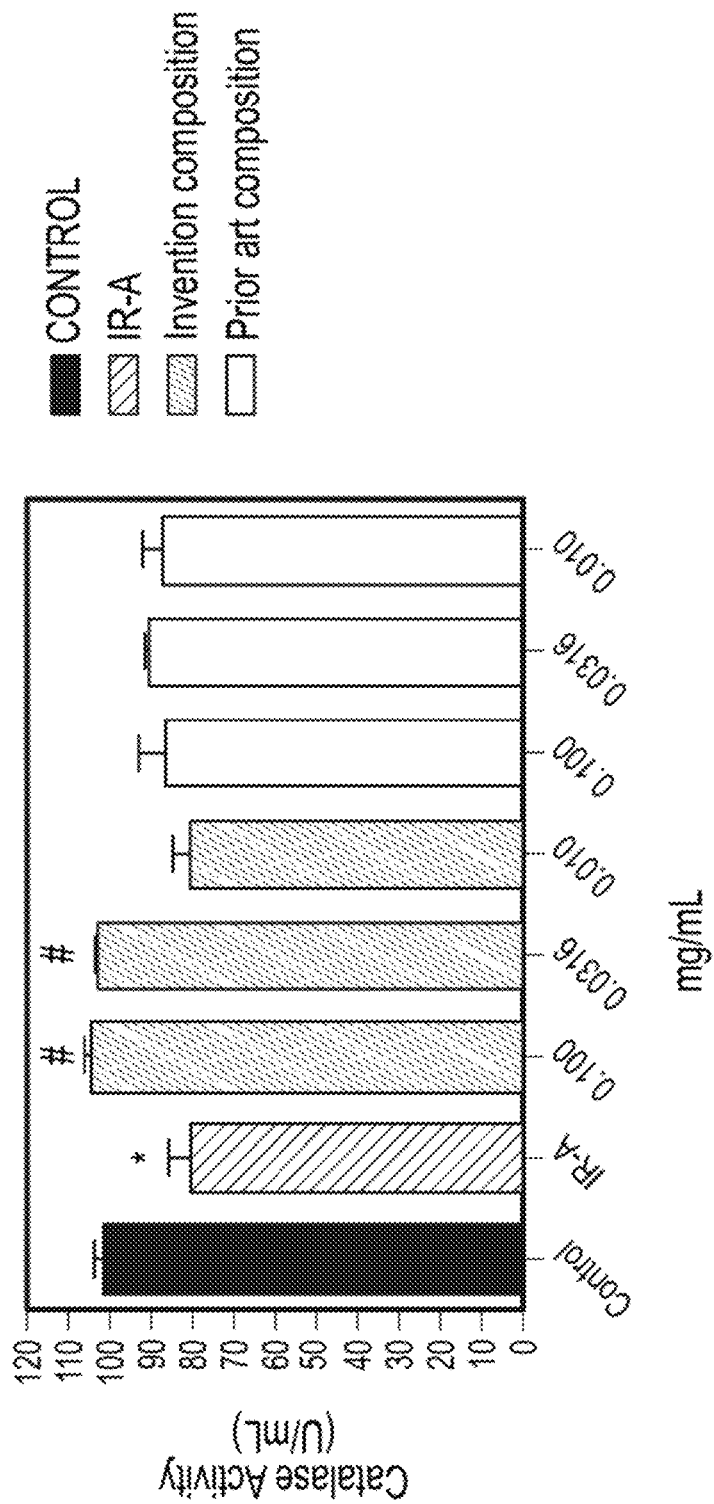

COMPOSITION COMPRISING CYCLODEXTRIN AS UV- AND IR-RADIATION SCREEN AGENT

The present invention relates to compositions, particularly topical compositions, comprising cyclodextrin as an agent for screening out solar UV and IR radiation.

BACKGROUND

Compositions comprising sun protection agents (embracing all different names such as sunscreen, sun or solar filter, sun block, antisun, photo protector and similars), are topical products aimed at interacting—e.g. absorbing or reflecting—with solar radiation incident on the skin or hair. Concerning the skin, the use of such compositions help protect against a number of various deleterious effects of radiation upon the skin, such as sunburn, premature ageing, wrinkles, loss of elasticity, photodermatitis and cancer.

In the text that follows, "skin products" or "sun protection products" are to be understood as aimed at be applied to skin or hair, irrespectively of the intended use, such as cosmetic, cosmeceutical or medical.

Different sun protection agents comprised in skin products have different ways of dealing with the sun light in order to provide "sun protection", e.g. by chemically absorbing the radiation or by physically blocking out the radiation.

In the following text, "sun protection products" is indicative of both, products that aim specifically at providing sun protection, as well as multi-functional products such as anti-ageing, face or body treatment products, make-up, shampoo, etc., that comprise as an additional benefit ingredient a sun protection agent.

Sun protection compositions are often presented as emulsions, be it of oil-in-water type (i.e. a cosmetically and/or dermatologically acceptable support consisting of an aqueous dispersing continuous phase and of a fatty dispersed discontinuous phase), or water-in-oil type (aqueous phase dispersed in a continuous fatty phase), which contain, in varying concentrations, one or more standard lipophilic organic screening agents and/or metal oxide mineral nanopigments capable of selectively absorbing/reflecting harmful UV radiation, such screening agents (and the amounts thereof) being selected as a function of the desired sun protection factor (SPF). Such ingredients are not known to provide relevant protection against IR radiation.

A list with non-limitative examples of additives in sun protection products that chemically absorb UV radiation is as follows: aminobenzoic acid, avobenzone, benzophenone, cinoxate, dioxybenzone, ensulizole, homosalate, meradimate, octisalate, octinoxate, octocrylene, PABA (p-amino benzoic acid), sulisobenzone, trolamine salicylate.

A list with non-limitative examples of additives in sun protection products that physically block out UV radiation comprises the following metallic oxides: iron, titanium, cerium, zinc, aluminum, zirconium and silicon.

While most sun protection products screen out only UV-B rays, exposure to UV-A and IR radiations are responsible for premature ageing of the skin, including loss of elasticity of the skin and wrinkles. So the search for efficient wide spectrum radiation filters is an ongoing activity in the sun protection industry.

According to one aspect of the invention, cyclodextrin employed in a composition along with one or more UV radiation absorbers and/or one or more UV radiation blockers boosts their UV-protection effect. According to another aspect of the invention, cyclodextrin employed in a composition, alone or with one or more UV radiation absorbers and/or one or more UV radiation blockers provides IR-protection effect.

BRIEF DESCRIPTION OF THE INVENTION

As utilized in this text, unless otherwise expressly stated the references to "radiation absorber" or "radiation screen" are to be understood as a chemical agent's effect concerning protection against UV (ultraviolet) and IR (infrared) radiations. In the prior art, cyclodextrin is mostly mentioned as able to form inclusion/encapsulation complexes or adducts, that is, certain chemical compounds can be entrapped on a hydrophobic cavity provided by the shape of the cyclodextrin molecule.

Related to sun protection products cyclodextrin is also mentioned in different contexts. For instance:

U.S. Pat. No. 6,428,796, WO2008003685, FR2756487—emulsion stabilizer;

DE10141683—mixtures of cyclodextrin and metal oxides such as $TiO_2$, ZnO, $Al_2O_3$, etc., in dermatological light protection preparations, to obtain reduced tack and greasiness;

DE19718318—mentions that compositions comprising organic sun filters, such as dibenzoylmethane derivatives and/or cinnamic acid derivatives, are less subject to UV destabilization in the presence of cyclodextrin, despite the fact that "the cyclodextrins are not characterized by significant light absorption in the UV range." This prior art teaches away from the invention.

U.S. Pat. No. 5,514,367—cosmetic compositions for artificially tanning the skin containing at least (a) an effective amount of a skin tanning agent; (b) at least one cyclodextrin; and (c) a cosmetically acceptable carrier.

It has now been found that cyclodextrin can be used as an efficient physical agent for avoiding the harmful effects of UV and IR radiation, totally or partially replacing known physical UV absorbers, such as metal oxides, particularly of titanium or zinc.

Adequate cyclodextrins, according to the invention, not excluding any other, is one or more of the following:

α-cyclodextrin: 6-membered sugar ring molecule

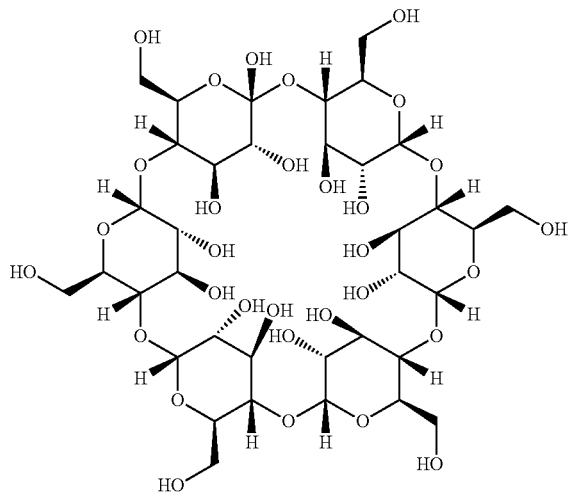 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@](O)(O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

β-cyclodextrin: 7-membered sugar ring molecule

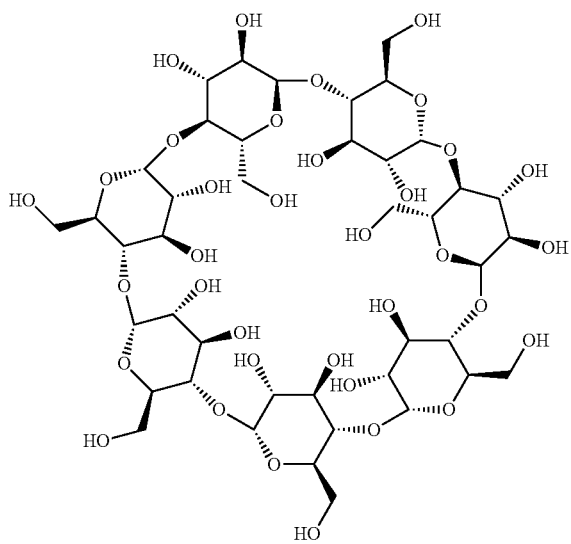 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

γ-cyclodextrin: 8-membered sugar ring molecule

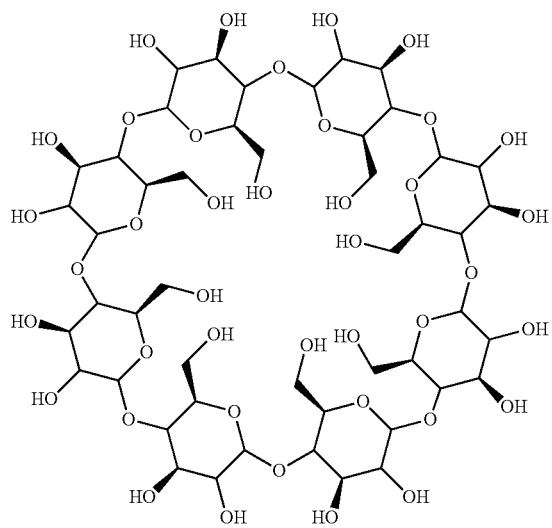 [SMILES: OC[C@H]1OC2OC3[C@H](O)C(O)C(OC4[C@H](O)C(O)C(OC5[C@H](O)C(O)C(OC6[C@H](O)C(O)C(OC7[C@H](O)C(O)C(OC8[C@H](O)C(O)C(OC9[C@H](O)C(O)C(OC1[C@H](O)C2O)O[C@@H]9CO)O[C@@H]8CO)O[C@@H]7CO)O[C@@H]6CO)O[C@@H]5CO)O[C@@H]4CO)O[C@@H]3CO]

In particular embodiments of the invention, beta-cyclodextrin is the cyclodextrin used.

UV and IR protection compositions comprising cyclodextrin according to the invention can be of any physical form known to the person skilled in the art, such as aerosols, creams, gels, lotions, emulsions, powder, foam, ointment, etc.

In particular embodiments, the compositions of the invention are oil-in-water or water-in-oil emulsions, aqueous or anhydrous gel, more particularly an oil-in-water emulsion.

When a composition according to the invention is an oil-in-water emulsion (o/w), it will typically include ingredients generally used for preparing emulsions such as, but not limited to, non ionic surfactants well known in the art to prepare o/w emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

The particle size of cyclodextrin used in the compositions of the invention is chosen according to the envisaged formulation, as known to the person skilled in the art. Typically, without excluding any other range, a useful cyclodextrin particle size is within the 0.1 μm to 1000 μm range, more particularly within the 10 μm to 500 μm range. Depending on the particular application, cyclodextrin can be added in amounts from 1 to 40 weight percent based on the total weight of the composition, particularly 2 to 30 weight percent on the same basis, more particularly 5 to 30 weight percent on the same basis.

The manner to incorporate the particulate cyclodextrin to any skin composition or formulation is also known to the person skilled in the art.

The bases for the compositions of the invention, and manners to prepare them, are known in art. A known publication about sun screen technology and formulations is "Sunscreens: Development: Evaluation, and Regulatory Aspects", Lowe, N. J. et al., Marcel Dekker, 2nd edition, 1997.

The compositions according to the invention may be applied onto an animal body, typically a human body, by any proper method of application, with cosmetic, cosmeceutical or medical finalities. Such compositions may be applied to skin or hair, using applicators, brushes or similar devices, or by hand, by pouring and rubbing or massaging the composition on the body surface. For use on the skin, the compositions according to the invention may be used in a conventional manner for example for conditioning the skin. An effective amount of the composition is applied to the skin, effective amounts generally ranging for instance from about 0.5 mg/cm$^2$ to about 3 mg/cm$^2$. Application to the skin typically includes a certain amount of working the composition onto the skin. This method for applying the composition of the invention on the skin comprises the steps of contacting the skin with the composition, preferably in an effective amount, and then spreading or rubbing the composition on the surface of the skin.

Compositions according to present invention may comprise ingredients listed in the CTFA INCI (Cosmetic, Toiletry and Fragrance Association, International Nomenclature of Cosmetic Ingredients) dictionary. Alternatively, the composition may comprise at least one of the following active ingredients: an anti-acne agent, antidandruff agent, antifungal agent, antimicrobial agent, antioxidant, biocide, external analgesic, oxidizing agent, reducing agent, skin bleaching agent, pigments, moisturizers, vitamins, enzymes, optical brighteners, surfactants, fragrances, preservatives, vitamins and their derivatives, whitening agents, ceramides, aminoacid derivatives, liposomes, polyols, such as glycerine and propylene glycol, botanicals (plant extracts), conditioning agents for hair and skin such as quaternary polymers or silicone materials such as aminofunctional silicones, humectants, preservatives, emollients, occlusive agents, antimicrobial agents, antifungal agents, antiviral agents, insect repellents, foam boosting agents, agents for artificially tanning and/or browning the skin (self-tanning agents), electrolytes, pH control agents, oxidative and non oxidative hair colorants, fixative resins, film formers, powders, and glittering agents.

The compositions according to this invention can be used on humans or animals.

Another aspect of the invention is a skin or hair treatment providing UV and IR sun protection wherein the composition of the invention is spread on the skin or hair of the subject to be treated.

EXAMPLES

The following examples aim to provide particular embodiments of the invention, but they do not, in any way, limit the invention more strictly than the attached claims.

Example 1

A Prior Art SPF 30 Sunscreen Formulation

| | COMPONENT TABLE | |
|---|---|---|
| | INGREDIENT | w/w % |
| A | water | Qsp 100 |
| | Disodium EDTA | 0.05 |
| | Glycerin | 1.50 |
| | Triethanolamine | 0.04 |
| | Acrylic Acid/VP Crosspolymer (UltraThix ™-P100) | 0.40 |
| B | Butyl Methoxydibenzoylmethane (Escalol ™ 517) | 3.50 |
| | Ethylhexyl salicylate (Escalol ™ 587) | 3.00 |
| | Octocrylene (Escalol ™ 597) | 7.00 |
| | Glyceryl Stearate and Laureth-23 (Cerasynt 945) | 1.50 |
| | Tridecyl Neopentanoate (Ceraphyl ™ 55) | 3.00 |
| | VP/Eicosene Copolymer (Antaron ™ V-220) | 2.00 |
| | Titanium Dioxide/Phenethyl Benzoate/Isocetyl Stearoyl Stearate (Escalol ™ Block) | 5.00 |
| | Bis-ethylhexyloxyphenol methoxyphenyl triazine (Escalol ™ S) | 3.30 |
| | Homosalate | 9.50 |
| C | Potassium Cetyl phosphate | 1.50 |
| D | Triethanolamine | 0.25 |
| E | Cyclopentasiloxane (Si-Tech ® CM 040) | 0.50 |
| F | Disodium lauriminodiproprionate tocopheryl phosphates (Vital ET ™) | 0.50 |
| | Phenoxyethanol (and) caprylyl glycol (Optiphen ™) | 0.80 |
| | 96% Denatured alcohol | 1.50 |

4—At 83-88° C., add phase C into phase AB, and mix for about 10 minutes. Agitate in the turrax for 5 minutes.
5—Add phase D and homogenize for 5 minutes.
6—At 40° C. add phase E and homogenize for 5 minutes.
7—Cool to 35-30° C., add phase F and homogenize for 10 minutes.
Obtained product:
Aspect: Yellowish emulsion
pH: 6.2-7.2;
Viscosity: 15.000-90.000 cps (Brookfield DV I, F 4, 0.6 rpm, 25° C.).

Example 2

A SPF 30 Sunscreen Formulation According to the Invention

| | COMPONENT TABLE | |
|---|---|---|
| | INGREDIENT | W/W % |
| A | water | Qsp 100 |
| | Disodium EDTA | 0.05 |
| | Glycerin | 1.50 |
| | Triethanolamine | 0.04 |
| | Acrylic Acid/VP Crosspolymer (UltraThix ™-P100) | 0.40 |
| B | Butyl Methoxydibenzoylmethane (Escalol ™ 517) | 3.50 |
| | Ethylhexyl salicylate (Escalol ™ 587) | 3.00 |
| | Octocrylene (Escalol ™ 597) | 7.00 |
| | Glyceryl stearate and laureth-23 (Cerasynt 945) | 1.50 |
| | Tridecyl neopentanoate (Ceraphy ™ 55) | 3.00 |
| | VP/Eicosene Copolymer (Antaron ™ V-220) | 2.00 |
| | Bis-ethylhexyloxyphenol methoxyphenol triazine (Escalol ™ S) | 3.30 |
| | Homosalate | 9.50 |
| C | Potassium Cetyl phosphate | 1.50 |
| D | Triethanolamine | 0.25 |
| E | Cyclopentasiloxane (Si-Tech ® CM 040) | 0.50 |
| F | Disodium lauriminodiproprionate tocopheryl phosphates (Vital ET ™) | 0.50 |
| | Phenoxyethanol (and) caprylyl glycol (Optiphen ™) | 0.80 |
| | 96% Denatured alcohol | 1.50 |
| | Beta cyclodextrin (*) | 5.0 |

(*) average particle size 118 μm

Procedure and obtained product—as described in example.

Example 3

Comparison Between Prior Art and an Invention Composition Concerning UV Protection Using the COLIPA (European Cosmetics Association) 2011 methodology, SPF and PF-UVA were determined for both compositions (prior art and invention).

The results are presented in the table below:

| FORMULATION | SPF | PF-UVA | WAVELENGTH (nm) |
|---|---|---|---|
| Example 1 (prior art) | 32, 1 | 17, 67 | 379 |
| Example 2 (invention) | 34, 3 | 25, 19 | 381 |

As can be seen, the use of cyclodextrin as physical UV absorber, according to the invention, gives efficient general UV protection, and very good UV-A protection.

Example 4

IR Protection Comparison Between Prior Art and Invention Compositions

As known in the art, a common event after exposure of skin to IR radiation is the formation of free radicals, such as superoxides and hydroxyl radicals, through the so-called oxidative phosphorilation process, which causes damage to lipidic and proteic cell constituents, and mainly to nucleic acids. Aiming to revert such oxidative damage, a homeostase redox mechanism is utilized by the cells, consisting in the balance between the production of free radicals and their elimination by antioxidant enzymes, such as catalase. So catalase was used to evaluate the effect of IR of the tested samples, as follows.

Human Fibroblast Culture

Human fibroblast HFF-1 (ATCC SCRC-1041, Rio de Janeiro cell bank Cat. 0275) were seeded in 75 cm² bottles (Nunc A/S, Denmark), cultivated and expanded in an incubator at 37° C. under 5% $CO_2$ atmosphere, using adequate culture medium. When confluence was reached, the cells were seeded in 6-well plates (Nunc A/S, Denmark) for incubation of the tested samples, exposure to radiation and catalase quantification.

Incubation of Cultures with Tested Samples and Irradiation

The cell cultures were incubated with three earlier determined non-toxic concentrations for the tested samples according to example 1 (prior art composition) and example 2 (invention composition) namely 0.100 mg/mL, 0.0316 mg/mL e 0.010 mg/mL. The cells were kept in touch with the tested samples for 24 hours. After that period the cells were submitted to a 360 J/cm² dose of infrared-A radiation with the help of a Hydrosun 750 irradiator (Hydrosun Medizintechnik GmbH, Müllheim, Germany). The infrared-A irradiance rate was calculated with the help of a HBM 1 measuring instrument (Hydrosun Medizintechnik GmbH, Müllheim, Germany) and detected a spectral radiation of 172 mW/cm2, resulting from the exposure of the cultures for 35 minutes. The cells were then incubated for additional 48 hour with the tested samples. After that period, the cell lisate was collected for the quantification of catalase.

Catalase Quantification

The catalase activity was measured in the cell lisate of the cultures using an assay kit provided by Cayman Chemical Co., USA. The measuring method is based on the reaction of the enzyme with methanol in the presence of hydrogen peroxide ($H_2O_2$) that generates formaldehyde, which is then detected with the addition of the chromogen 4-amino-3-hidrazino-5-mercapto-1,2,4-triazol. The catalase activity is calculated based on the known standard concentration of formaldehyde (μM), using the following equation: catalase activity (nmol/min/mL)=μM of sample/20 minutes. One catalase unit is defined as the amount of enzyme that promotes the formation of 1 nmol/minute of formaldehyde. The absorbance was read at 540 nm in a monochromator Multiskan GO (Termo Scientific, USA).

Statistical Evaluation

The statistical evaluation made use of the ANOVA "F" test to measure the variation of the obtained results, comparing the data from the samples. As the F test was positive for the significant variation among the results, the non-parametric Tukey test was employed, which reinforced and made more precise the results obtained in the F test. Significance level was 5%. The software employed was SPSS 20, commercialized by IBM, USA.

Results

The results shown on FIG. 1 are representative of the infrared A radiation (IR-A) upon the production of catalase in cultures of human fibroblasts.

BRIEF DESCRIPTION OF THE FIGURES

Further embodiments of the present application can be understood with reference to the appended FIGURE.

The graph shows on FIG. 1 shows the effects of infrared radiation A on the production of the catalase enzyme in the human fibroblast culture. As can be seen, IR-A radiation imposed a significant reduction of 20.82% (P<0.05) on the catalase activity when compared to the non-irradiated base control. This indicates the harmful effect of IR-A on the unbalance of cutaneous photo-damage.

On the other hand the tested samples showed protective effect on the cell cultures, avoiding the reduction on the activity of the antioxidante catalase enzyme. The composition of the invention, in the concentrations of 0.100 mg/mL and 0.0316 mg/mL promoted increase of 31.78% and 27.08%, respectively, in the activity of catalase, as compared to the group submitted to IR-A radiaton. While the invention composition presents protection of catalase enzyme activity, the prior art composition did not promote significant protection of the catalase enzyme activity.

With reference to the statistical model utilized: in the graph above the symbol "#" means that the invention tested samples, in concentrations of 0.100 mg/mL and 0.0316 mg/mL, presented effects with statistically significant difference concerning the control, that is, the unprotected IR-A exposed sample. None of the other samples presented statistically significant differences.

A person skilled in the art will promptly appreciate, based on the teachings contained in the text and examples herein, advantages of the invention, and will be able to propose equivalent embodiments of the invention, comprising variations and alternatives, without departing from the scope of the invention according to the attached claims.

The invention claimed is:

1. A UV (Ultraviolet)-A and IR (Infrared)-A radiation screen composition comprising:
    a cyclodextrin particulate consisting of beta-cyclodextrin as a physical UV-A or IR-A filter for sun radiation;
    a non-ionic surfactant; and
    one or more UV radiation absorbers,
    wherein:
        the particle of the beta-cyclodextrin particulate have an average particle size of about 10 μm to about 500 μm,
        the composition does not include any metal oxides, and the composition is an oil-in-water emulsion and is provided as a lotion, an aerosol, a cream, a gel, a foam, or an ointment, and
        the beta-cyclodextrin comprises about 5 to about 30% of the total composition.

2. The composition according to claim 1, wherein the composition is applied to a skin or hair of humans or animals.

3. The composition according to claim 1, wherein the composition is an anti-aging product, a face treatment product, a body treatment product, a make-up product or a shampoo product.

4. A method of skin treatment comprising applying the composition of claim 1 upon the skin or hair of the humans or animals to be treated.

5. The method of claim 4, wherein the amount of the composition applied on the skin or hair ranges from about 0.5 mg/cm² to about 3 mg/cm².

6. The composition of claim 1, wherein the non-ionic surfactant is selected from the group consisting of polyoxyethylene alkyl ether, a polyoxyethylene alkylphenol ether, a polyoxyethylene lauryl ether, a polyoxyethylene sorbitan monoleate, a polyoxyethylene alkyl ester, a polyoxyethylene sorbitan alkyl ester, a polyethylene glycol, a polypropylene glycol, a diethylene glycol, an ethoxylated trimethylnonanol, a polyoxyalkylene glycol modified polysiloxane, and mixtures thereof.

7. The composition of claim 1, further comprising at least one of an anti-acne agent, an antidandruff agent, an antifungal agent, an antimicrobial agent, an antioxidant, a biocide, an external analgesic, an oxidizing agent, a reducing agent, a skin bleaching agent, a pigment, a moisturizer, a vitamin, an enzyme, an optical brightener, a fragrance, a preservative, a vitamin, a vitamin derivative, a whitening agents, a ceramide, an amino-acid derivative, a liposome, a polyol, a botanical, a conditioning agent, a humectant, a preservative, an emollient, an occlusive agent, an antimicrobial agent, an antifungal agent, an antiviral agent, an insect repellent, a foam boosting agent, artificial tanning agent, an electrolyte, a pH control agents, an oxidative hair colorant, a non-oxidative hair colorant, a fixative resin, a film former, a glittering agent, or a mixture thereof.

8. The composition of claim 1, wherein the one or more UV radiation absorbers are selected from the group consisting of aminobenzoic acid, avobenzone, benzophenone, cinoxate, dioxybenzone, ensulizole, homosalate, meradimate, octisalate, octinoxate, octocrylene, PABA (p-amino benzoic acid), sulisobenzone, trolamine salicylate, and combinations thereof.

9. A UV (Ultraviolet)-A and IR (Infrared-A) radiation screen composition comprising:
a cyclodextrin particulate consisting of beta-cyclodextrin as a physical UV-A or IR-A filter for sun radiation;
a non-ionic surfactant, and
a denatured alcohol
wherein:
the particle of the beta-cyclodextrin particulate have an average particle size of about 10 μm to about 1000 μm, and the composition is an oil-in-water emulsion and is provided as a lotion, an aerosol, a cream, a gel, a foam, or an ointment, and
the beta-cyclodextrin comprises about 5 to about 30% of the total composition.

* * * * *